United States Patent [19]

Matsubara et al.

[11] 4,223,015
[45] Sep. 16, 1980

[54] COMPOSITION FOR TREATING SKIN DISEASES

[75] Inventors: Masaka Matsubara, A-1001 Yushima-haitaun, 4/6/11, Yushima, Bunkyo-ku, Tokyo-to, Japan; Tatsuo Ishihara; Tokitaka Mori, both of Tokyo, Japan

[73] Assignee: Masaka Matsubara, Tokyo, Japan

[21] Appl. No.: 780,020

[22] Filed: Mar. 22, 1977

[30] Foreign Application Priority Data

Mar. 31, 1976 [JP] Japan .................................. 51-34291

[51] Int. Cl.² ............................................ A61K 35/56
[52] U.S. Cl. ............................................ 424/95
[58] Field of Search ......................... 424/95

[56] References Cited

PUBLICATIONS

Chemical Abstracts 73: 28906f (1970).

*Primary Examiner*—Jerome D. Goldberg
*Attorney, Agent, or Firm*—Toren, McGeady and Stanger

[57] ABSTRACT

A process for preparing a parenteral solution for treating skin diseases comprising the steps of:
  (1) freeze-drying an aqueous extract of paramecium to obtain a dry powder $P_1$,
  (2) dissolving the dry powder $P_1$ in water and separating the aqueous solution into a high-molecular-weight portion A and a low-molecular-weight portion B,
  (3) freeze-drying an aqueous solution of the portion B to obtain a dry powder $P_2$, and
  (4) dissolving the dry powder $P_2$ in an excipient to formulate the parenteral solution.

8 Claims, No Drawings

COMPOSITION FOR TREATING SKIN DISEASES

This invention relates to a composition for treating skin diseases and to a process for preparing the same.

We conducted research by extracting paramecium with water or an aqueous solution, adding alcohol or acetone to the extract and dissolving the resulting precipitate in water. We have further continued the research and found that when the extract of paramecium with water or aqueous solution is separated into a high-melecular-weight portion (which may be referred to as "portion A") and a low-molecular-weight portion (which may be referred to as "portion B"), these portions have different properties. More specifically stated, we have found the following. When the portion A is used for treatment in the human body, the proper therapeutic dose thereof is close to a dose which is harmful to the body, hence hazardous. In contrast, the portion B is free of such drawbacks, has higher activity than the portion A and, unlike the portion A, produces an outstanding effect to cure skin diseases. We have also confirmed that the following steps, characteristic of this invention, are essential to the preparation of the composition contemplated by the invention.

This invention provides a composition for treating skin diseases which are difficult to cure and a process for preparing the composition, the process comprising, in combination, the steps of:

(1) freeze-drying an aqueous extract of paramecium to obtain a dry powder $P_1$, (2) dissolving the dry powder $P_1$ in water and separating the aqueous solution into a high-molecular-weight portion A and a low-molecular-weight portion B, (3) freeze-drying an aqueous solution of the portion B to obtain a dry powder $P_2$, and (4) dissolving the dry powder $P_2$ in an excipient to formulate a parenteral solution.

The proper dose of the composition of this invention for therapeutic uses can be determined with ease and is harmless to the human body. The present composition is highly effective in curing skin diseases. The mode of such outstanding action of the present composition, although still remaining to be clarified, presumably belongs to immunotherapy which has drawn increased attention in recent years. The use of the present composition has caused no leukopenia in any case, nor does it produce any objectionable side effect. The efficacy thereof on skin diseases appears to be attributable also to their ability to activate lymphocytes (T-cells).

The parameciums to be used in this invention are protozoans, and any protozoan of the genus Paramecium is usable. Examples of useful parameciums are *Paramecium aurelia, Paramecium bursaria, Paramecium calkinsi, Paramecium caudatum, Paramecium multimieulonueleatum, Paramecium polycaryum, Paramecium trichium, Paramecium woodruffi* and *Killer Paramecium*.

The paramecium is extracted with water, which may contain buffer agents or a pH adjusting agent, such as hydrochloric acid, acetic acid, NaOH or the like. These agents are used in a small amount usually less than 1%. The water may further contain a harmless organic or inorganic substance, such as ethyl alcohol, phosphate, etc. in a small amount. For the extraction, the paramecium is placed into a glass container and brought into contact with water usually at 0° C. to 100° C., preferably at about 70° C. to about 90° C. After completion of the extraction, the mixture is cooled and then divided into a supernatant (extract) and a precipitate by centrifuging. The precipitate may further be subjected to extraction in the same manner as above. When the extraction procedure is followed at least twice, the resulting extracts are combined and then freeze-dried to obtain a dry powder.

The step of freeze-drying and the paramecium extract (hereinafter referred to as "the first freeze-drying step") to prepare a dry powder $P_1$ can be carried out in a usual manner. For example, the dry powder can be obtained by freezing the extract with a mixture of dry ice and acetone, liquefied air or the like, and subjecting the frozen mass to a reduced pressure not higher than the water-vapor pressure of the mass to thereby remove the water upon sublimation. When the first freeze-drying step is eliminated from the process of this invention, the freeze-dried powder to be thereafter obtained is soluble in water only with difficulty, giving a considerable amount of insolubles even when heated. Accordingly, the first freeze-drying step is essential to the present process in permitting the dry powder resulting from the second freeze-drying step to completely dissolve in water.

The powder prepared by the first freeze-drying step is then dissolved in water, and the aqueous solution is separated into a high-molecular-weight portion A and a low-molecular-weight portion B. The method of the separation is not particularly limited but may be any of the various methods given below. The separation can be effected to any desired degree. Examples of useful separation methods are:

(a) Dialysis

The aqueous solution of freeze-dried powder $P_1$ is dialyzed with use of a dialysis membrane, such as Visking Tubing (trade mark for a cellulose tube manufactured by Visking Company, U.S.A.). The high-molecular-weight portion A remaining in the membrane is removed, and the low-molecular-weight portion B passing outward through the membrane is collected.

(b) Ultrafiltration

The aqueous solution of freeze-dried powder $P_1$ is separated by an ultrafilter into a high-molecular-weight portion A not passing through the filter and a low-molecular-weight portion B passing through the filter. Several kinds of ultrafilters are commercially available for the separation of varying molecular weights, such as Diafilter (trade mark of Bioengineering Co., Ltd., Japan), Diaflofilter (trade mark of Amicon Corporation, U.S.A.), Satorius ultrafilter UCF (trade mark of Satorius Co., Ltd., West Germany), Millipore pellicon ultrafilter PSAC (Millipore Co., Ltd., U.S.A.).

(c) Gel filtration

The aqueous solution of freeze-dried powder $P_1$ is passed through a column filled with a gel filtration agent. The high-molecular-weight portion A flowing out first is discarded, and the low-molecular-weight portion B thereafter flowing out is collected. Available as gel filtration agents are Sephadex (trade mark of Pharmacia Fine Chemical, Sweden), Biogel (trade mark of Biorad Co., Ltd., U.S.A.).

(d) Separation with use of organic solvent

The aqueous solution of freeze-dried powder $P_1$ is admixed with an organic solvent highly miscible with water, in an amount of several times the amount of the solution to precipitate the high-molecular-weight portion A. The supernatant, namely the low-molecular-weight portion B, separated from the precipitate is concentrated at a reduced pressure. Examples of useful organic solvents are methanol, ethanol, acetone etc.

According to the present invention, the low-molecular-weight portion B thus prepared is freeze-dried to obtain a dry powder $P_2$. (This step will hereinafter be referred to as "the second freeze-drying step".) This step is carried out in the same manner as the first freeze-drying step.

The composition of this invention contains the dry powder $P_2$ as the effective component thereof. It is prepared as a parenteral solution which is administered subcutaneously. The desired parenteral solution is formulated in the usual manner, namely by weighing out a specified amount of the freeze-dried powder $P_2$ and dissolving the powder in an excipient, suited for parenteral solutions, such as water, physiological saline solution or the like already known.

The therapeutically proper dose of the parenteral solution of this invention is readily determinable by experts. The parenteral solution of this invention preferably contains the portion B in a concentration of about 0.01–1.0 wt./vol. % for the therapy.

The portion B of this invention has the following properties shown below in Tables 1 and 2, which also indicate those of the portion A.

TABLE 1

|  | Portion B | Portion A |
|---|---|---|
| Solubility |  |  |
| in water | soluble | soluble |
| in ethanol | soluble | insoluble |
| in ethyl ether | insoluble | insoluble |
| Utraviolet absorption | Max. Absorption at 240–280 mµ (specific extinction: 9.5) | Max. Absorption at 240–280 mµ (specific extinction: 45.6) |
| Molecular weight | predominantly up to 5,000 | predominantly at least 5,500 |

TABLE 2

| Reaction | Qualitative reaction | |
|---|---|---|
|  | Portion B | Portion A |
| Molisch | (++) | (+) |
| Nylander | (++) | (+) |
| Anthron | (++) | (+) |
| Biuret | (+) | (+) |
| Orien —HCl | (++) | (+) |
| Rhodamin | (+) | (+) |
| Somogyi | (+++) | (+) |
| Diphenylamine | (+) | (−) |
| Solfosalicylicacid | (−) | (−) |
| Nynhidrin | (++) | (+) |
| Phenol —$H_2SO_4$ | (++) | (+) |

These results appear to indicate that the portion B consists predominantly of sugar protein containing nucleic acid.

This invention will be described below with reference to Examples.

EXAMPLE 1

A suspension of paramecium in water, frozen for preservation, is thawed. The pH of the suspension is adjusted to about 5.5, and the suspension is thereafter heated for one hour on a water bath at 70° C. with stirring. The suspension is cooled and separated into a supernatant (extract) and a precipitate by centrifuging. A suitable amount of water is added to the precipitate, and the pH of the mixture is adjusted to the same level as above. The mixture is then heated for one hour on a water bath at 80° C. with stirring. The precipitate obtained in the same manner as above by centrifuging is similarly heated on a water bath at 90° C. The three extracts thus obtained are combined and concentrated at a reduced pressure to obtain a concentrate.

Subsequently, the concentrate is frozen with a mixture of dry ice and acetone and then freeze-dried at a reduced pressure of 3 mm Hg to obtain a dry powder $P_1$. A 0.9 g quantity of the powder $P_1$ is dissolved in 50 ml of water, and the solution is placed into a Visking Tubing. The tube is placed into 500 ml of water, subjecting the solution to dialysis at 5° C. for 48 hours, whereby an outer solution is obtained. The tube is further placed in 500 ml of fresh water to conduct dialysis at 5° C. for 24 hours and to thereby obtain another outer solution.

The combined outer solutions are concentrated to about 50 ml at a reduced pressure, and the concentrate is treated in the same manner as above, giving 195 mg of a freeze-dried powder $P_2$.

The powder $P_2$ is formulated into a 0.2 wt./vol. % aqueous solution as a parenteral solution of this invention.

EXAMPLE 2

A 1.3 g quantity of the freeze-dried powder $P_1$ prepared in Example 1 is dissolved in 50 ml of water. The solution is placed into an ultrafiltration device equipped with an ultrafilter, Diaflo UM-10 (separation melecular weight: 10000). While being subjected to pressure of 4 kg/cm² by nitrogen gas, the solution is concentrated to such an extent that the amount of the solution on the ultrafilter has reduced to 10 ml. Water (50 ml) is then added to the remaining solution, and the resulting solution is further filtered. When the amount of the solution has been reduced to 15 ml, the filtrate is withdrawn from the device and treated in the same manner as in Example 1, giving 540 mg of freeze-dried powder $P_2$.

The powder $P_2$ is formulated into a 0.2 wt./vol. % aqueous solution as a parenteral solution of this invention.

EXAMPLE 3

A 1.5 g quantity of the freeze-dried powder $P_1$ prepared in Example 1 is dissolved in 10 ml of water. The solution is placed into a column, 2.5 cm in diameter and 38 cm in length, filled with a gel filtration agent, i.e. Sephadex G-25. Distilled water is then poured into the column to obtain a filtrate, which is collected by a fraction collector in 5-ml fractions. The fractions are each analyzed by ultraviolet spectrophotometry (involving an absorption at 260 mµ due to the presence of nucleic acid) and also by phenol sulfuric acid method (for the qualitative reaction of sugar). Based on the results, the fractions are grouped into the following four peaks.

| Peak No. | Fraction No. | Yield (mg) | |
|---|---|---|---|
| 1 | 16–25 | 142 | A |
| 2 | 26–42 | 500 | ⎫ |
| 3 | 46–55 | 9 | ⎬ B |
| 4 | 56–65 | 10 | ⎭ |

Peak No. 1 is a portion A, and Peak Nos. 2–4 are portion B. The portion B is freeze-dried in the same manner as in Example 1 to obtain 519 mg of a dry powder $P_2$.

The powder $P_2$ is formulated into a 0.2 wt./vol. % aqueous solution as a parenteral solution of the invention.

EXAMPLE 4

A 7 g quantity of the freeze-dried powder $P_1$ prepared in Example 1 is dissolved in 140 ml of water, and 700 ml of ethanol is added to the solution. After being allowed to stand overnight in a cold atmosphere, the resulting solution is centrifuged at 10000 r.p.m. for 15 minutes and is thereby separated into a supernatant and a precipitate. Water (50 ml) is added to the precipitate, and 250 ml of ethanol is further added to the solution obtained. The resulting solution is then refrigerated overnight and centrifuged at 10000 r.p.m. for 15 minutes. The supernatant separated from the precipitate is combined with the supernatant obtained by the first centrifuging step. The combined supernatants are concentrated at a reduced pressure. The concentrate is freeze-dried in the same manner as in Example 1, giving 4.973 g of dry powder $P_2$.

The powder $P_2$ if formulated into a 0.2 wt./vol. % aqueous solution as a parenteral solution of this invention.

Biological activity of the parenteral solution of the invention

Effects on difficultly curable skin diseases (a) The parenteral solution of this invention, prepared in Example 3, was subcutaneously administered every other day at a dose of 1 ml to patients with the disease listed in Table 5, which also shows the results. The table reveals that effective cases reach 94.2%.

TABLE 5

| Diagnosis | Number of cases | Effect | | |
|---|---|---|---|---|
| | | Highly effective | Effective | Ineffective |
| Pustulosis palmaris et plantaris | 26 | 23 | 3 | 0 |
| Pruritus senilis | 23 | 21 | 2 | 0 |
| Trichophytia Pompholyciformis | 105 | 103 | 2 | 0 |
| Psoriasis vulgaris | 4 | 0 | 4 | 0 |
| Behçet disease | 2 | 0 | 2 | 0 |
| Verruca vulgaris | 9 | 9 | 0 | 0 |
| Acne vulgaris | 20 | 9 | 6 | 5 |
| Total | 189 | 165 | 13 | 5 |
| | | 178(94.2%) | | |

Pustulosis palmaris et plantaris, arising from causes not known, is still thought to be incurable by medicine. However, the parenteral solution of this invention, when administered to patients with this disease, effected a complete cure in one to two months. Pruritus senilis, whose cause also remains to be determined, is difficult to cure, causing painful itching to the patient day and night, notwithstanding that the skin has no pathologic change whatever. The medicine at the present level provides nothing effective in curing such patients, whereas the parenteral solution of this invention achieved surprising efficacies on the patients.

Similarly, trichophytia pompholyciformis is widely known to be difficult to cure, and drugs have yet to be explored which will completely cure the disease. Nevertheless, patients with this disease, when given the parenteral solution, can be cured completely in about one month.

The parenteral solution of this invention also produces outstanding effects on Behçet disease and psoriasis vulgaris which are included in the difficultly curable diseases heretofore known.

What is claimed is:

1. A process for preparing a parenteral solution for treating the following diseases:

pustulosis palmaris et plantaris, pruritus senilis, trichophytia pompholyciformis, psoriasis vulgaris, Behcet disease, verruca vulgaris, or acne vulgaris, comprising
    (1) freeze-drying an aqueous extract of paramecium to obtain a dry powder $P_1$,
    (2) dissolving the dry powder $P_1$ in water and separating the aqueous solution into a high-molecular-weight portion A and a low-molecular-weight portion B,
    (3) freeze-drying an aqueous solution of the portion B to obtain a dry powder $P_2$, and
    (4) dissolving the dry powder $P_2$ in an excipient to formulate the parenteral solution, the amount of dry powder $P_1$ used being sufficient to provide a parenteral solution of $P_2$ of a concentration from about 0.01 to 1.0 wt./vol. percent.

2. A process as defined in claim 1 wherein the portion B is soluble in water, ethanol and insoluble in ethyl ether, has a maximum absorption at 240–280 m$\mu$ in ultraviolet spectrophotometry and has a molecular weight of predominantly up to 5,000.

3. A process as defined in claim 1 wherein the aqueous solution of the dry powder $P_1$ is separated by dialysis.

4. A process as defined in claim 1 wherein the aqueous solution of the dry powder $P_1$ is separated by ultrafiltration.

5. A process as defined in claim 1 wherein the aqueous solution of the dry powder $P_1$ is separated by gel filtration.

6. A process as defined in claim 1 wherein the aqueous solution of the dry powder $P_1$ is separated with use of an organic solvent selected from the group consisting of methanol, ethanol, and acetone.

7. A parenteral solution for treating difficultly curable skin diseases prepared by the process defined in claim 1.

8. A method of treating pustulosis palmaris et plantaris, pruritus senilis, trichophytia pompholyciformis, psoriasis vulgaris, Behcet disease, verruca vulgaris, or acne vulgaris by administering the parenteral solution defined in claim 7 to the patient in an amount effective to minimize the effects of the disease.

* * * * *